(12) United States Patent
Heasman et al.

(10) Patent No.: US 12,432,509 B2
(45) Date of Patent: *Sep. 30, 2025

(54) OBJECTIVE DETERMINATION OF ACOUSTIC PRESCRIPTIONS

(71) Applicant: Cochlear Limited, Macquarie University (AU)

(72) Inventors: John Michael Heasman, Hampton (AU); Kerrie Plant, Melbourne (AU); Peter Gibson, South Coogee (AU); Stephen O'Leary, Melbourne (AU); Luke Campbell, Melbourne (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/621,924

(22) Filed: Mar. 29, 2024

(65) Prior Publication Data

US 2024/0323625 A1   Sep. 26, 2024

Related U.S. Application Data

(63) Continuation of application No. 17/963,713, filed on Oct. 11, 2022, now Pat. No. 11,979,719, which is a
(Continued)

(51) Int. Cl.
*A61B 5/00* (2006.01)
*A61B 5/12* (2006.01)
(Continued)

(52) U.S. Cl.
CPC ............. *H04R 25/70* (2013.01); *A61B 5/125* (2013.01); *A61N 1/0541* (2013.01);
(Continued)

(58) Field of Classification Search
CPC .... A61B 5/125; A61B 5/7264; A61N 1/0541; A61N 1/36036; A61N 1/36038; A61N 1/36039
See application file for complete search history.

(56) References Cited

U.S. PATENT DOCUMENTS 8,170,678 B2   5/2012   Polak
8,265,765 B2   9/2012   Nicolai et al.
(Continued)

FOREIGN PATENT DOCUMENTS

KR   100974153 B1   8/2010

OTHER PUBLICATIONS

T.Y.C. Ching, et al., "Binaural-Bimodal Fitting or Bilateral Implantation for Managing Severe to Profound Deafness: A Review", Trends in Amplification, vol. 11, No. 3, Sep. 2007, 32 pages.
(Continued)

*Primary Examiner* — Jon Eric C Morales
(74) *Attorney, Agent, or Firm* — Edell, Shapiro & Finnan, LLC

(57) ABSTRACT

Presented herein are techniques that make use of objective measurements obtained in response to acoustic stimulation signals. More specifically, at least one measure of outer hair cell function and at least one measure of auditory nerve function are obtained from a tonotopic region of an inner ear of a recipient of a hearing prosthesis. The at least one measure of auditory nerve function and the least one measure of outer hair cell function are then analyzed relative to one another.

20 Claims, 12 Drawing Sheets

Related U.S. Application Data continuation of application No. 16/801,885, filed on Feb. 26, 2020, now Pat. No. 11,540,069, which is a continuation of application No. 15/299,707, filed on Oct. 21, 2016, now abandoned.

(51) Int. Cl.
    *A61N 1/05*     (2006.01)
    *A61N 1/36*     (2006.01)
    *H04R 25/00*     (2006.01)

(52) U.S. Cl.
    CPC ..... *A61N 1/36036* (2017.08); *A61N 1/36038* (2017.08); *H04R 25/356* (2013.01); *A61B 5/7264* (2013.01); *A61N 1/36039* (2017.08)

(56) References Cited

U.S. PATENT DOCUMENTS

| | | | |
|---|---|---|---|
| 9,155,886 | B2 | 10/2015 | James et al. |
| 11,540,069 | B2 * | 12/2022 | Heasman ............... H04R 25/70 |
| 11,979,719 | B2 * | 5/2024 | Heasman ........... A61N 1/36036 |
| 2010/0152813 | A1 | 6/2010 | Lineaweaver et al. |
| 2011/0064240 | A1 | 3/2011 | Litvak et al. |
| 2012/0109006 | A1 | 5/2012 | James et al. |
| 2014/0270291 | A1 | 9/2014 | Flynn et al. |
| 2015/0057714 | A1 | 2/2015 | Litvak et al. |
| 2016/0045749 | A1 | 2/2016 | James et al. |
| 2021/0186380 | A1 | 6/2021 | Liberman et al. |

OTHER PUBLICATIONS

Ward. R. Drennan, Ph. D., et al., "Validation of a Clinical Assessment of Spectral Ripple Resolution for Cochlear-Implant Users", published in final edited form as: Ear Hear, 2014; 35(3): e92-e98, doi: 10.1097/AUD.0000000000000009, 17 pages.

John A. Ferraro, "Electrocochleography: A Review of Recording Approaches, Clinical Applications, and New Findings in Adults and Children", Journal of the American Academy of Audiology, vol. 21, No. 3, Mar. 2010, doi: 10.3766/jaaa.21.3.2, 8 pages.

Kirill V. Nourski, et al., "Acoustic-electric interactions in the guinea pig auditory nerve: Simultaneous and forward masking of the electrically evoked compound action potential", Hearing Research, vol. 232, Issues 1-2, Oct. 2007, 33 pages.

Jin Xu, et al., "Cochlear View: Postoperative Radiography for Cochlear Implantation", The American Journal of Otology, Jan. 2000, vol. 21, Issue 1, 8 pages.

Ting Zhang, et al., "Cochlear dead regions constrain the benefit of combining acoustic stimulation with electric stimulation", Ear Hear, Jul.-Aug. 2014, doi: 10.1097/AUD.0000000000000032, 19 pages.

G. Keidser, et al., "The NAL-NL2 prescription procedure", Audiology Research 2011, vol. 1:e24, May 2011, 3 pages.

Luke Campbell, et al., "Cochlear Response Telemetry: Intracochlear Electrocochleography via Cochlear Implant Neural Response Telemetry Pilot Study Results", Otology & Neurotology, 36:399-405, 2014, Otology & Neurotology, Inc., 7 pages.

Brian C.J. Moore, "Dead Regions in the Cochlea: Conceptual Foundations, Diagnosis, and Clinical Applications", Ear & Hearing, vol. 25, No. 2, Apr. 2004, 19 pages.

International Search Report and Written Opinion in corresponding International Application No. PCT/IB2017/056368, mailed Feb. 13, 2018, 11 pages.

\* cited by examiner

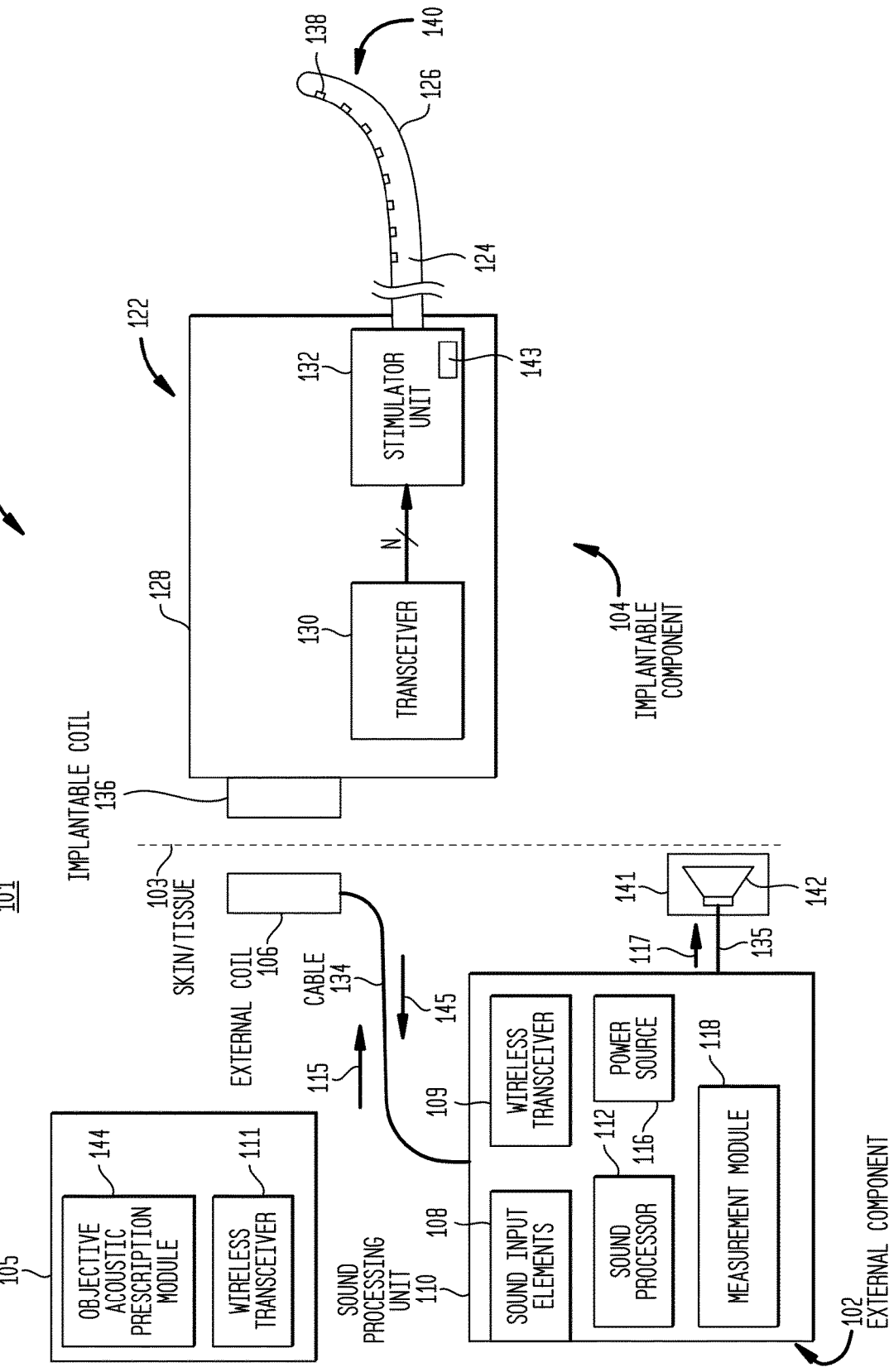

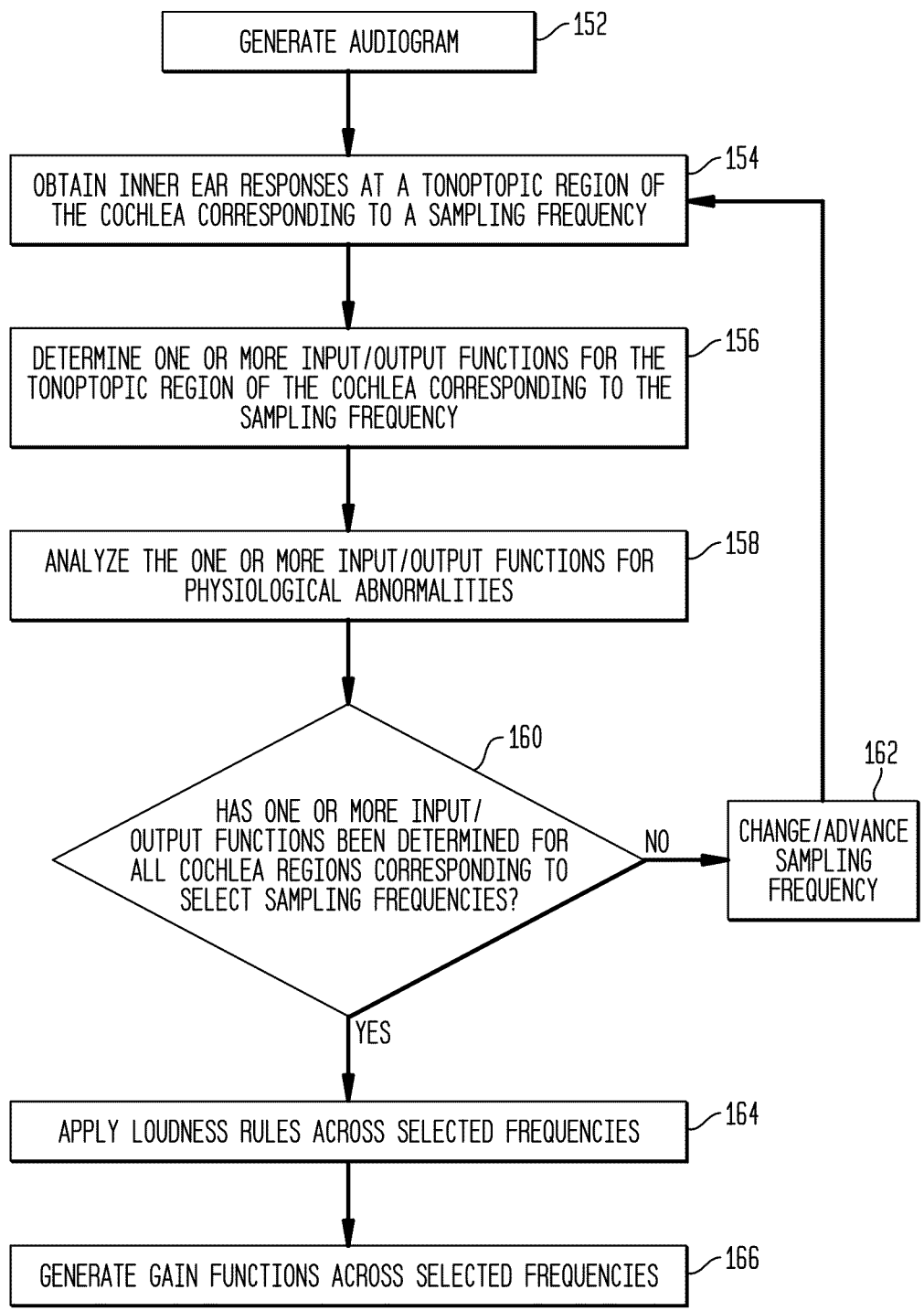

OBJECTIVE DETERMINATION OF ACOUSTIC PRESCRIPTIONS

CROSS-REFERENCE TO RELATED APPLICATION

This application is a continuation of U.S. patent application Ser. No. 17/963,713, filed Oct. 11, 2022, which is a continuation of U.S. patent application Ser. No. 16/801,885, filed Feb. 26, 2020, now U.S. Pat. No. 11,540,069, which is a continuation of U.S. patent application Ser. No. 15/299,707, filed Oct. 21, 2016, now Abandoned, the entire contents of which is incorporated herein by reference.

BACKGROUND

Field of the Invention

The present invention relates generally to electro-acoustic hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: obtaining a plurality of acoustically-evoked inner ear responses from an inner ear of a recipient of an electro-acoustic hearing prosthesis; determining, based on the plurality of acoustically-evoked inner ear responses, one or more input/output functions for at least one region of the inner ear; and determining, based on the one or more input/output functions, one or more gain functions for use by the electro-acoustic hearing prosthesis in conversion of sound signals to acoustic stimulation signals for delivery to the recipient.

In another aspect, an electro-acoustic hearing prosthesis system is provided. The electro-acoustic hearing prosthesis system comprises: an intra-cochlear stimulating assembly configured to be implanted in an inner ear of a recipient, wherein the intra-cochlear stimulating assembly comprises a plurality of stimulating contacts; and one or more processors configured to: obtain, via one or more of the plurality of stimulating contacts, objective inner ear responses to acoustic stimulation at one or more regions of the inner ear, generate, based on the objective inner ear responses to acoustic stimulation, a mapping of one or more relationships between the acoustic stimulation and an output functionality of the one or more regions of the inner ear, and generate, based on at least the mapping of one or more relationships between the acoustic stimulation and an output functionality of the one or more regions of the inner ear, an acoustic prescription for conversion of sound signals to acoustic stimulation signals for delivery to the recipient.

BRIEF DESCRIPTION OF THE DRAWINGS

Embodiments of the present invention are described herein in conjunction with the accompanying drawings, in which:

FIG. 1B is a block diagram of the hearing prosthesis system of FIG. 1A;

FIG. 4 is a detailed flowchart illustrating a method in accordance with embodiments presented herein;

DETAILED DESCRIPTION

Figure 1A:
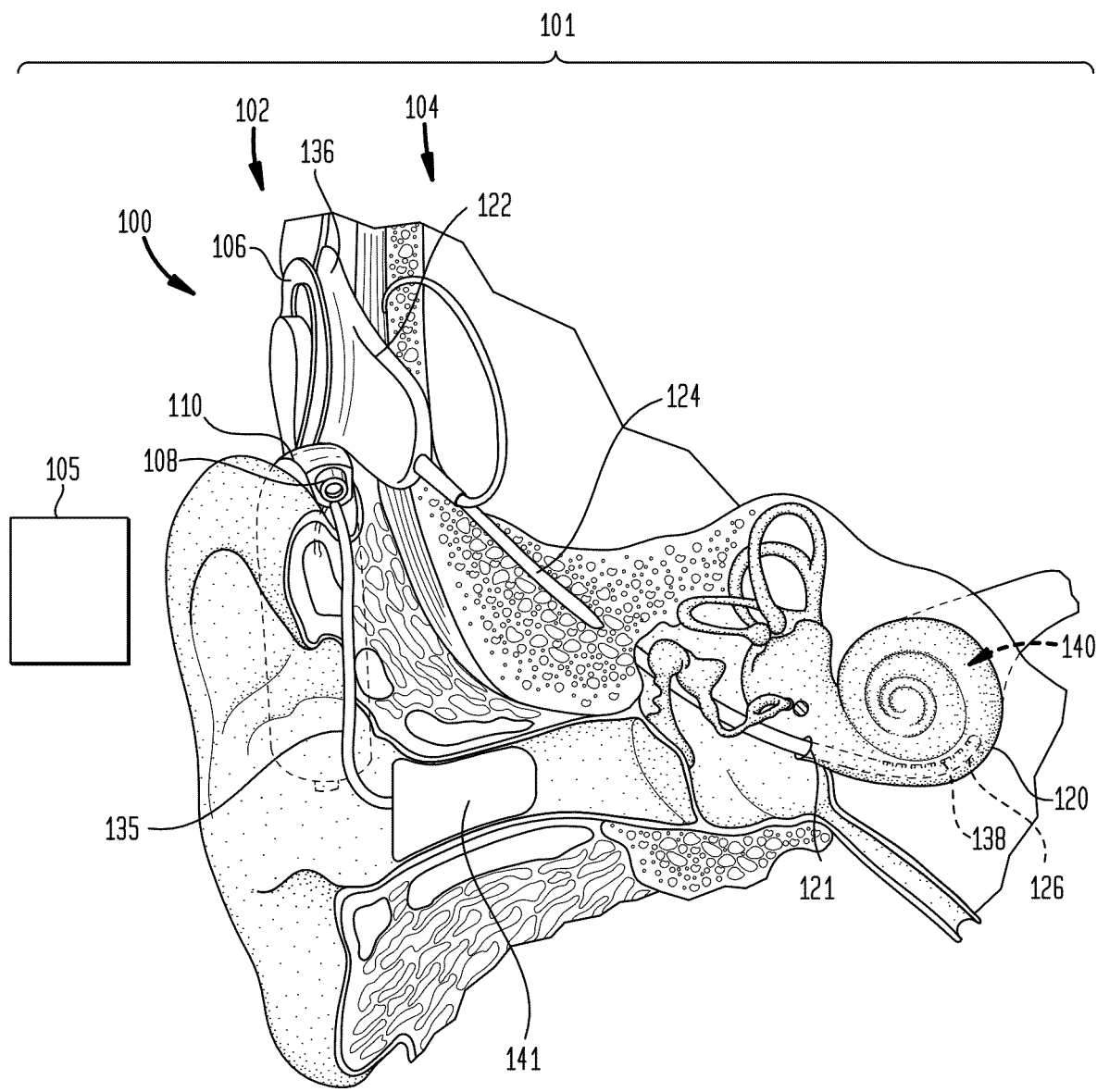
FIG. 1A is a schematic diagram of a hearing prosthesis system in accordance with embodiments presented herein.

Auditory/hearing prosthesis recipients suffer from different types of hearing loss (e.g., conductive and/or sensorineural) and/or different degrees/severity of hearing loss. However, it is now common for many hearing prosthesis recipients to retain some residual natural hearing ability (residual hearing) after receiving the hearing prosthesis. For example, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the higher frequency regions of the cochlea.

Due, at least in part, to the ability to preserve residual hearing, the number of recipients who are candidates for different types of implantable hearing prostheses, particularly electro-acoustic hearing prostheses, has continued to expand. Electro-acoustic hearing prostheses are medical devices that deliver both acoustic stimulation (i.e., acoustic stimulation signals) and electrical stimulation (i.e., electrical stimulation signals), possibly simultaneously, to the same ear of a recipient.

The cochlea is "tonotopically mapped," meaning that regions of the cochlea toward the basal region are responsive to higher frequency signals, while regions of the cochlea toward apical region are responsive to lower frequency signals. For example, the proximal end of the basal region is generally responsible to 20 kilohertz (kHz) sounds, while the distal end of the apical region is responsive to sounds at around 200 hertz (Hz). In hearing prosthesis recipients, residual hearing most often is present within the lower frequency ranges (i.e., the more apical regions of the cochlea) and little or no residual hearing is present in the higher frequency ranges (i.e., the more basal regions of the cochlea). This property of residual hearing is exploited in electro-acoustic hearing prostheses where the stimulating assembly is inserted into the basal region and is used to deliver electrical stimulation signals to evoke perception of higher frequency sound components, while acoustic stimulation is used to evoke perception of sound signal components corresponding to the lower frequencies of input sound signals (as determined from the residual hearing capabilities of the implanted ear). The tonotopic region of the cochlea where the stimulation output transitions from the acoustic stimulation to the electrical stimulation is called the crossover frequency/frequency region.

Electro-acoustic hearing prosthesis recipients typically benefit from having the acoustic stimulation in addition to the electrical stimulation, as the acoustic stimulation adds a more "natural" sound to their hearing perception over the electrical stimulation signals only in that ear. The addition of the acoustic stimulation can, in some cases, also provide improved pitch and music perception and/or appreciation, as the acoustic signals may contain a more salient lower frequency (e.g., fundamental pitch, F0) representation than is possible with electrical stimulation. Other benefits of electro-acoustic hearing prosthesis may include, for example, improved sound localization, binaural release from unmasking, the ability to distinguish acoustic signals in a noisy environment, etc.

The effectiveness of electro-acoustic and other hearing prostheses generally depends on how well a particular prosthesis is configured or "fit" to the recipient of the particular prosthesis. For instance, the "fitting" of a hearing prosthesis to a recipient, sometimes also referred to as "programming" creates a set of configuration settings, parameters, and other data (collectively and generally "settings" herein) that define the specific operational characteristics of the hearing prosthesis. In the case of electro-acoustic hearing prostheses, fitting determines how the prosthesis operates to convert portions (frequencies and/or frequency ranges) of detected sound signals (sounds) into electrical and acoustic stimulation signals. For example, the fitting process results in the determination of an "acoustic prescription" comprising one or more sets of gain functions that are used to map/translate received sound signals into output acoustic simulation levels.

Presented herein are techniques that make use of objective measurements, such as acoustically-evoked inner ear responses, in the fitting process to determine the patient-centric acoustic prescription (gain functions) that are used by an electro-acoustic hearing prosthesis to translate received sound signals into output acoustic simulation levels. More specifically, in accordance with the techniques presented herein a plurality of acoustically-evoked inner ear responses are obtained from an inner ear of a recipient of an electro-acoustic hearing prosthesis. One or more input/output functions for at least one region of the inner ear are determined based on the plurality of acoustically-evoked inner ear responses and the one or more input/output functions are, in turn, used to determine one or more gain functions for use by the electro-acoustic hearing prosthesis.

As described further below, the techniques presented herein create an acoustic prescription (i.e., a set of gain functions), which is primarily based on personalized measurements/responses of the recipient's inner ear, such as the auditory nerve neurophonic (ANN) and/or cochlear microphonic (CM), to acoustic stimulation signals. The auditory nerve neurophonic function, when correlated with the acoustic stimulation signals, provide a basic input/output function for a tonotopic region of the inner ear. This input/output function which is transformed into an acoustic prescription after applying various loudness rules. In certain embodiments, outer hair cell (OHC) function, as represented by the cochlear microphonic, are also obtained and correlated (e.g., compared) with the auditory nerve neurophonic. In these embodiments, the correlation of the outer hair cell function responses with the auditory nerve neurophonic can usefully identify mismatches which are then used to make further personalized adjustments to the prescription. For example, dead regions can be identified and taken into account, thereby leading to a superior prescription for each recipient.

For ease of illustration, embodiments are primarily described herein with reference to a hearing prosthesis system that includes an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.), etc.

FIGS. 1A and 1B are diagrams of an illustrative hearing prosthesis system 101 configured to implement the techniques presented herein. More specifically, FIGS. 1A and 1B illustrate hearing prosthesis system 101 that comprises an electro-acoustic hearing prosthesis 100 and an external device 105. The external device 105 is a computing device, such as a computer laptop, desktop, tablet), mobile phone, remote control unit, etc. For ease of description, the external device 105 is described as being a computer.

The implantable electro-acoustic hearing prosthesis 100 includes an external component 102 and an internal/implantable component 104. The external component 102 is configured to be directly or indirectly attached to the body of a recipient, while the implantable component 104 is configured to be subcutaneously implanted within the recipient (i.e., under the skin/tissue 103 of the recipient).

The external component 102 comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a wireless transceiver 109, a sound processor 112, a power source 116, and a measurement module 118. The sound processing unit 110 may be, for example, a behind-the-ear (BTE) sound processing unit, a body-worn sound processing unit, a button sound processing unit, etc.

Connected to the sound processing unit 110 (e.g., via a cable 135) is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation signals) to the recipient's inner ear via the outer ear, ear canal, and the middle ear.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intra-cochlear electrical stimulating contacts (electrodes) 138 that collectively form a contact array 140 for delivery of electrical stimulation (current) to the recipient's cochlea.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured execute sound processing and coding to convert the electrical input signals received from the sound input elements into output signals that represent acoustic and/or electric (current) stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustic stimulation signals to the recipient. As such, depending on a variety of factors, the sound processor 112 is configured to convert the electrical input signals received from the sound input elements into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the encoded data and power signals are received at the transceiver 130 and are provided to the stimulator unit 132. The stimulator unit 132 is configured to utilize the encoded data signals to generate electrical stimulation signals (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least one residual hearing). Therefore, the cochlea of a hearing prosthesis recipient can be acoustically stimulated upon delivery of a sound signal to the recipient's outer ear. In the example of FIGS. 1A and 1B, the receiver 142 is used to provide the acoustic stimulation. That is, the receiver 142 is configured to utilize the output signals 117 to generate acoustic stimulation signals that are provided to the recipient's cochlea via the middle ear bones and oval window, thereby creating waves of fluid motion of the perilymph within the cochlea.

Although FIGS. 1A and 1B illustrate the use of a receiver 142 to deliver acoustic stimulation to the recipient, it is to be appreciated that other types of devices may be used in other embodiments. It is also to be appreciated that embodiments of the present invention may be implemented in other hearing prostheses and other arrangements that that shown in FIGS. 1A and 1B. For example, it is to be appreciated that embodiments of the present invention may be implemented in fully-implantable hearing prostheses in which the sound processor, power supply, etc. are all implanted within a recipient so that the hearing prosthesis may operate, for at least a period of time, without the presence of an external component.

As noted, the electro-acoustic hearing prosthesis 100 also comprises the measurement module 118. As described further below, the measurement module 118 is configured to obtain one or more inner ear potentials/responses measured in-situ from the recipient's inner ear. As used herein, "inner ear potentials" refer to any voltage potential associated with either the electrical properties of the inner ear or its physiological function and/or potentials obtained via measurements at the inner ear. Potentials of a physiological nature (i.e., potentials relating to the physiological function of the inner ear), include acoustically-induced responses/potentials (e.g., electrocochleography (ECoG) responses) and electrically-induced responses/potentials (e.g., electrically evoked compound action potential (ECAP) responses. Other potentials of a physiological nature are referred to herein as higher evoked potentials, which are potentials related to the brainstem and auditory cortex, inclusive of the electrical auditory brainstem responses (EABR), the middle latency response, and cortical responses. Potentials of a physiological nature are sometimes referred to herein as "physiological potentials." Potentials of electrical nature (i.e., potentials relating to the electrical properties of the inner ear itself or intra-cochlear contacts) include voltage tomography responses, measured impedances (bulk and interface), and/or other forms of electrode (stimulating contact) voltage measurements. Potentials of electrical nature are sometimes referred to herein as "physiological electrical potentials."

As described further below, certain embodiments of the present invention make use of acoustically-evoked inner ear responses, such as ECoG responses, that are generated in a recipient's inner ear in response to the delivery of acoustic stimulation to the cochlea. A captured set of acoustically-evoked inner ear response may include a plurality of different stimulus related potentials, such as the cochlear microphonic (CM), the cochlear summating potential (SP), the auditory nerve neurophonic (ANN), and the auditory nerve or Compound Action Potential (CAP), which are measured independently or in various combinations.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The cochlear microphonic is a fluctuating voltage that mirrors the waveform of the acoustic stimulus at low, moderate, and high levels of acoustic stimulation. The cochlear microphonic is generated by the outer hair cells (OHCs) of the organ of Corti and is dependent on the proximity of the recording electrode(s) to the stimulated hair cells and the basilar membrane. In general, the cochlear microphonic is proportional to the displacement of the basilar membrane by the travelling wave phenomena and reflects/represents the outer hair cell function.

Figure 2A:
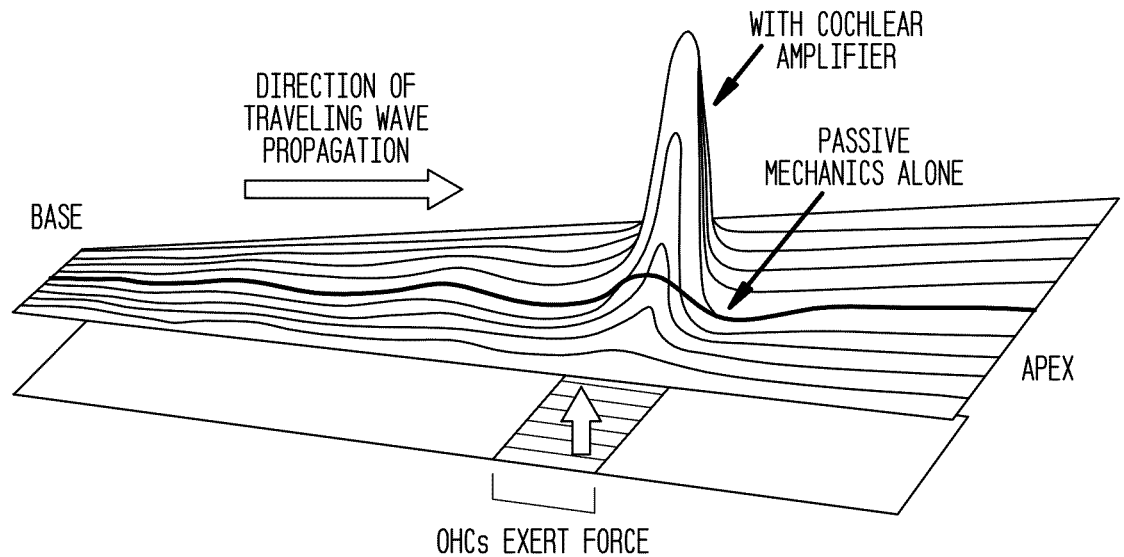
FIGS. 2A, 2B, 2C, and 2D are schematic diagrams illustrating operation of a recipient's inner ear.
Figure 2B:
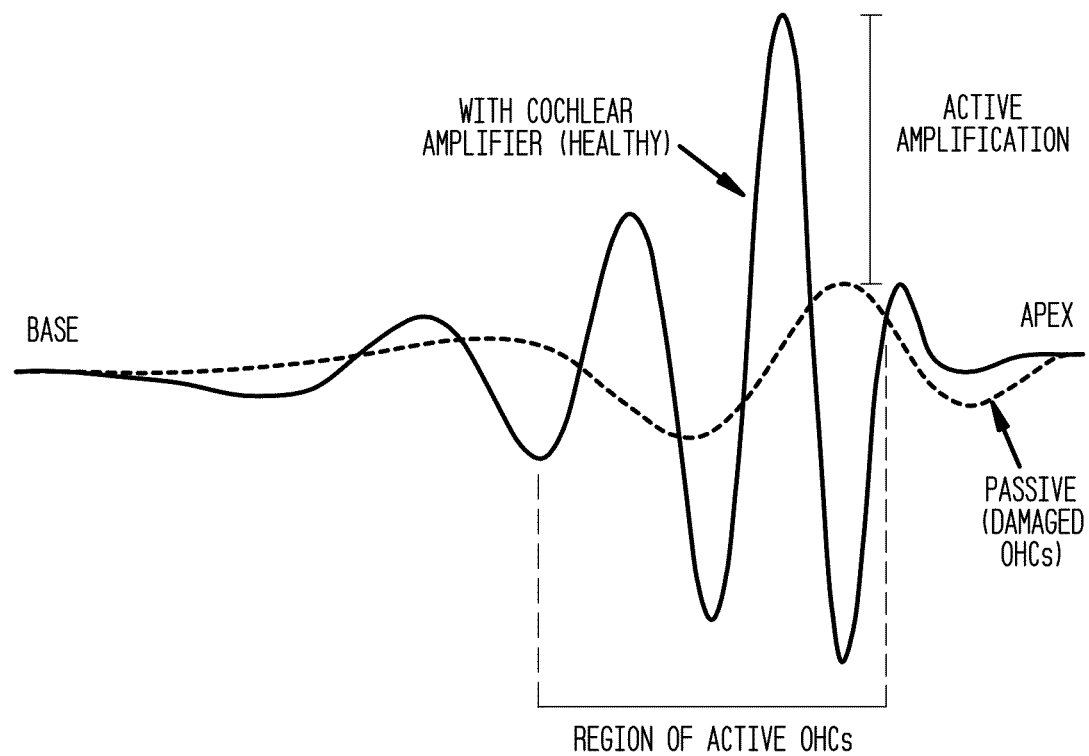
Figure 2C:
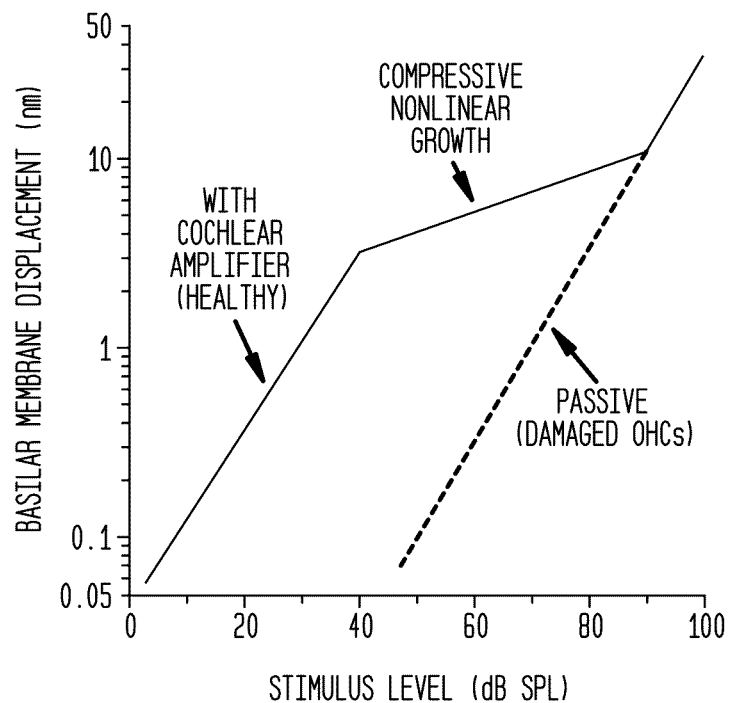
Figure 2D:
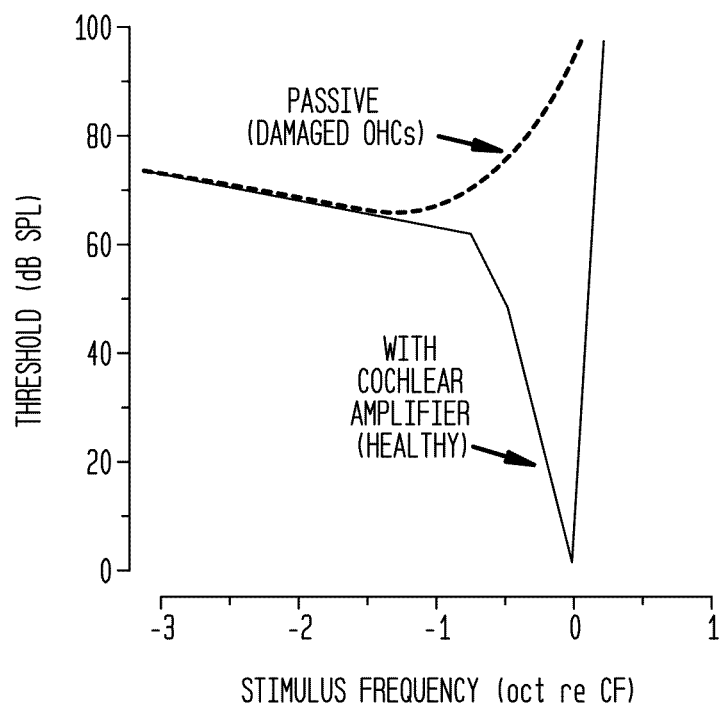

More specifically, the outer hair cells possess electromotility, a quality that can generate rapid and significant forces on the basilar membrane by the cell structure lengthening and contracting with sensory input from the auditory nerve. As shown in FIGS. 2A and 2B, this electromotility permits the cochlea to serve as an amplifier for sounds, thereby providing a non-linear compressive nature for input sounds. However, as shown in FIGS. 2C and 2D, the cochlea amplifier input/output function across a frequency can be compromised by a hearing impairment.

The signal throughput from the outer hair cell activity to the inner hair cell activity can be further compromised by the synaptic connections to the auditory nerve, as characterized by the auditory nerve neurophonic (ANN). The auditory nerve neurophonic is a signal recorded from the auditory nerve in response to the acoustic stimulation signals and represents the auditory nerve neurophonic function.

The auditory nerve Action Potential represents the summed response of the synchronous firing of the nerve fibers in response to the acoustic stimuli, and it appears as an alternating current voltage. The auditory nerve Action Potential is characterized by a series of brief, predominantly negative peaks, including a first negative peak (N1) and second negative peak (N2). The auditory nerve Action Potential also includes a magnitude and a latency. The magnitude of the auditory nerve Action Potential reflects the number of fibers that are firing, while the latency of the auditory nerve Action Potential is measured as the time between the onset and the first negative peak (N1).

Figure 3:
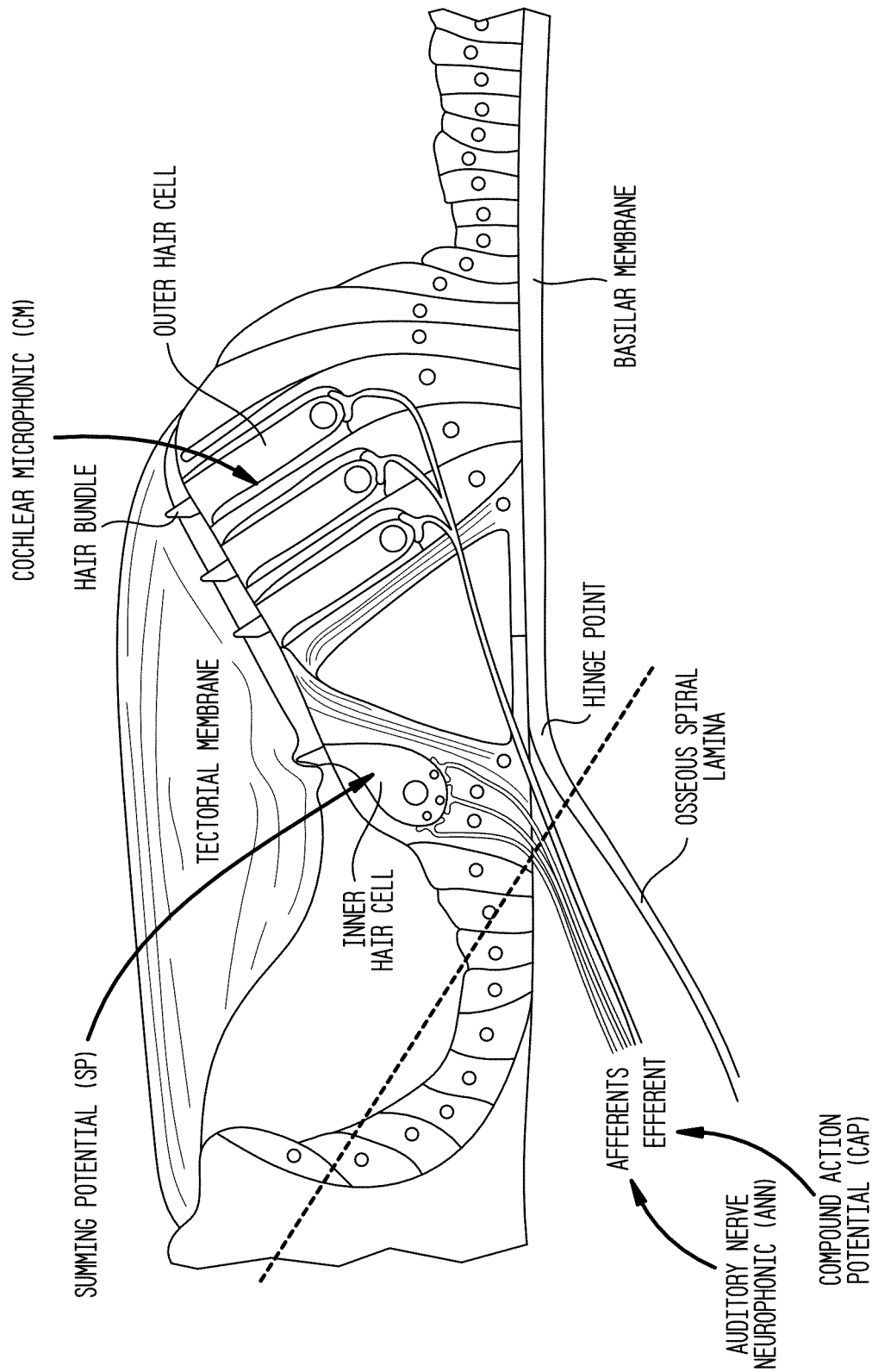
FIG. 3 is a schematic diagram illustrating a portion of a recipient's inner ear.

FIG. 3 is a schematic diagram illustrating the physiology of a portion of recipient's inner ear. FIG. 3 has also been labeled to illustrate where each of the cochlear microphonic (CM), the cochlear summating potential (SP), the auditory nerve neurophonic (ANN), and the auditory nerve or Compound Action Potential (CAP) are generated in the inner ear.

Returning to examples of FIGS. 1A and 1B, the measurement module 118 is configured to provide the obtained inner ear potentials to the computer 105. In one embodiment, computer 105 includes a wireless transceiver 111 that is configured to wirelessly communicate with the wireless transceiver 109 of the sound processing unit 110 to obtain/receive the inner ear potentials. In other embodiments, the computer 105 is physically connected to the sound processing unit 110 (e.g., via a port or interface of the sound processing unit and one or more interfaces of the computer) so as to receive the inner ear potentials over a wired connection. As described further below, upon obtaining the inner ear potentials, an objective acoustic prescription module 144 of the computer 105 is configured to use the inner ear potentials to generate one or more input/output functions for tonotopic regions of the cochlea. Using these input/output functions, as well as one or more loudness rules, the objective acoustic prescription module 144 generates an acoustic prescription (e.g., one or more sets of gain functions) for use by the electro-acoustic hearing prosthesis 100 to convert sound signal components into acoustic stimulation signals. That is, once generated, the acoustic prescription is provided to, and subsequently used by, the electro-acoustic hearing prosthesis 100

The objective generation of the acoustic prescription improves the operation of the electro-acoustic hearing prosthesis 100 and optimizes (e.g., personalizes) the gain functions for the recipient. That is, an acoustic prescription created using the techniques presented herein is highly personalized for the recipient due to the close and direct connections with the unique auditory biology of each recipient, and is also independent of the physical characteristics of the ear canal which can vary from recipient to recipient and which can lead to errors in conventional techniques for determining gain functions (i.e., does not require third party real-ear verification hardware for fitting quality control as required in conventional fitting practices).

In addition, an acoustic prescription created using the techniques can be substantially, and possibly fully, automated and relies upon minimal significant subjective feedback from the recipient (i.e., minimal interaction with the recipient). This makes the techniques presented suitable for children and or other recipients that may be unable to provide reliable subjective feedback. Moreover, certain embodiments facilitate detection of, and accommodation for, dead regions and other physiological abnormalities.

FIGS. 1A and 1B illustrate an arrangement in which the objective acoustic prescription module 144 is located at an external device 105. It is also to be appreciated that the objective acoustic prescription module 144 may implemented as part of the electro-acoustic hearing prosthesis 100 (e.g., as part of sound processing unit 110).

Furthermore, FIGS. 1A and 1B illustrate an arrangement in which the electro-acoustic hearing prosthesis 100 includes an external component 102. However, it is to be appreciated that embodiments of the present invention may be implemented in hearing prostheses having alternative arrangements. Similarly, FIGS. 1A and 1B illustrate the use of a receiver 142 to deliver acoustic stimulation to obtain acoustically-evoked inner ear responses. However, embodiments of the present invention may be implemented in other hearing prostheses that deliver stimulation in a different manner to evoke an acoustically-induced potential measurement (e.g., bone conduction devices or direct acoustic stimulators that deliver vibration to the cause pressure changes within the cochlea fluid).

FIG. 4 is a flowchart illustrating a method 150 in accordance with embodiments presented herein. For ease of illustration, the method 150 of FIG. 4 will be described with reference to the electro-acoustic hearing prosthesis system 101 of FIGS. 1A and 1B.

Method 150 begins at 152 where an audiogram measurement of the recipient's cochlea 140 is performed in order to record the recipient's residual hearing (i.e., to determine the frequency and/or frequency range where the recipient's residual hearing begins). An audiogram measurement refers to a behavioral hearing test, sometimes referred to as audiometry, which generates an audiogram. The behavioral test involves the delivery of different tones, presented at a specific frequency (pitch) and intensity (loudness), to the recipient's cochlea and the recording of the recipient's subjective responses. The resulting audiogram is a graph that illustrates the audible threshold for standardized frequencies as measured by an audiometer. In general, audiograms are set out with frequency in Hertz (Hz) on the horizontal (X) axis, most commonly on a logarithmic scale, and a linear decibels Hearing Level (dBHL) scale on the vertical (Y) axis. In certain arrangements, the recipient's threshold of hearing is plotted relative to a standardized curve that represents 'normal' hearing, in dBHL. The audiogram is used to determine the frequency and threshold of hearing for the recipient's cochlea.

At 154, the objective acoustic prescription module 144 obtains a plurality of acoustically-evoked inner ear responses at a selected sampling frequency. More specifically, acoustic stimulation signals (e.g., acoustic tones pure tones) are delivered, at the sampling frequency, to the recipient's outer ear using, for example, the receiver 142. The acoustic stimulation signals delivered by the receiver 142 cause displacement waveforms that travel along the basilar membrane and which rise to potentials. Therefore, in response to the delivered acoustic signals, one or more of the stimulating contacts 138 and the integrated amplifier(s) 143 of the cochlear implant capture one or more windows of the evoked activity (i.e., perform ECoG measurements) to generate acoustically-evoked inner ear responses (e.g., ECoG responses), which are generally represented in FIG. 1B by arrow 145, are transmitted back to the sound processing unit 110 and then forwarded to the external device 105.

The acoustic stimulation signals delivered at 154 have a certain/selected frequency, referred to as the sampling frequency. The sampling frequency remains constant, but the level/amplitude of the acoustic stimulation signals is changed to obtain a plurality of different sets of responses. In other words, the operations at 154 include the delivery of acoustic stimulation signals at incremental adjusted (e.g., incrementally increasing) amplitudes, but at a constant frequency.

As noted above, a recipient's cochlea is tonotopically mapped such that regions of the cochlea toward the basal region are responsive to higher frequency signals, while regions of cochlea toward the apical region are responsive to lower frequency signals. Also as noted above, in an electro-acoustic hearing prosthesis, such as prosthesis 100, acoustic stimulation is used to stimulate the frequencies below the cross-over frequency. As such, in accordance with the embodiments of FIG. 4, the sampling frequency is a frequency at which acoustic stimulation signals are expected to be delivered to the recipient (i.e., a frequency below the cross-over frequency).

At 156, the objective acoustic prescription module 144 is configured to use the plurality of inner ear responses obtained at 154 to determine one or more input/output (I/O) functions for the tonotopic region of the cochlea that corresponds to the sampling frequency, sometimes referred to herein as the sampled cochlea region. In general, the one or more input/output functions generated at 156 represent a mapping of one or more relationships between the acoustic signals delivered to the cochlea and an output functionality of the one or more regions of the inner ear (e.g., measured auditory nerve neurophonics). In certain embodiments, at least one input/output function is generated based on an analysis of measured auditory nerve neurophonics in relation to attributes of the delivered acoustic stimulation signals. In further embodiments, at least one output function is generated based on an analysis of measured cochlear microphonics (outer hair cell function) in relation to the attributes (e.g., amplitude) of the delivered acoustic stimulation signals.

The I/O functions may be calculated/determined in a number of different manners in either the time or frequency domain whereby both the input and output measures are consistent and a measurement of the signal amplitude or power is made. In one example, a time-domain RMS value of the input and output signal may be determined as the I/O function.

Figure 5A:
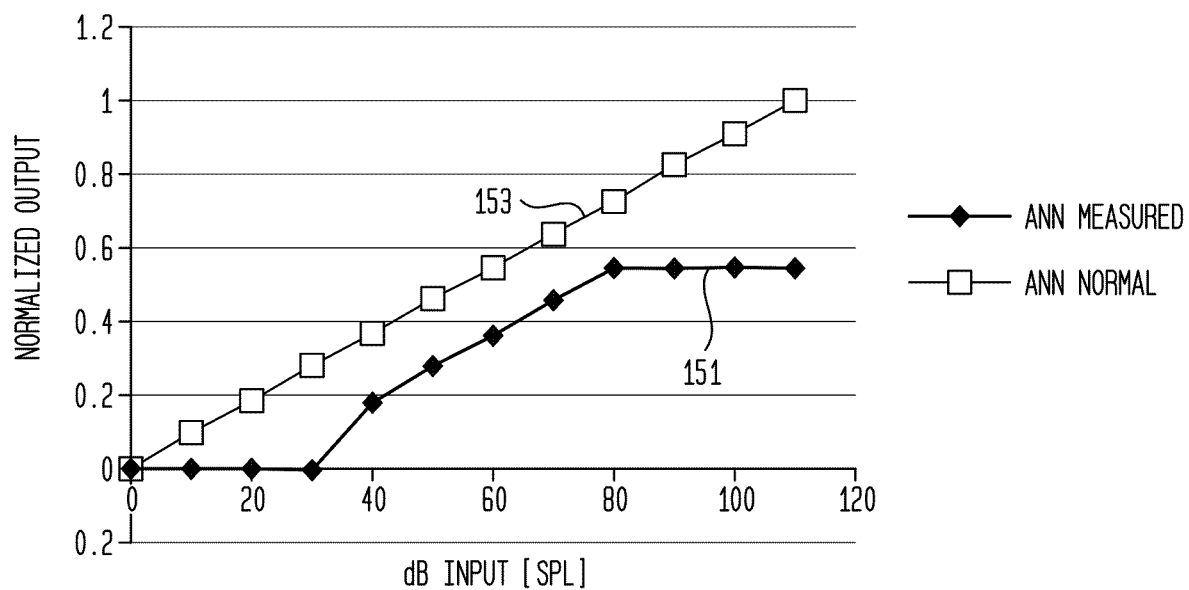
FIG. 5A is a graph illustrating measured auditory nerve neurophonic (ANN) outputs and normal/expected auditory nerve neurophonic outputs.
Figure 5B:
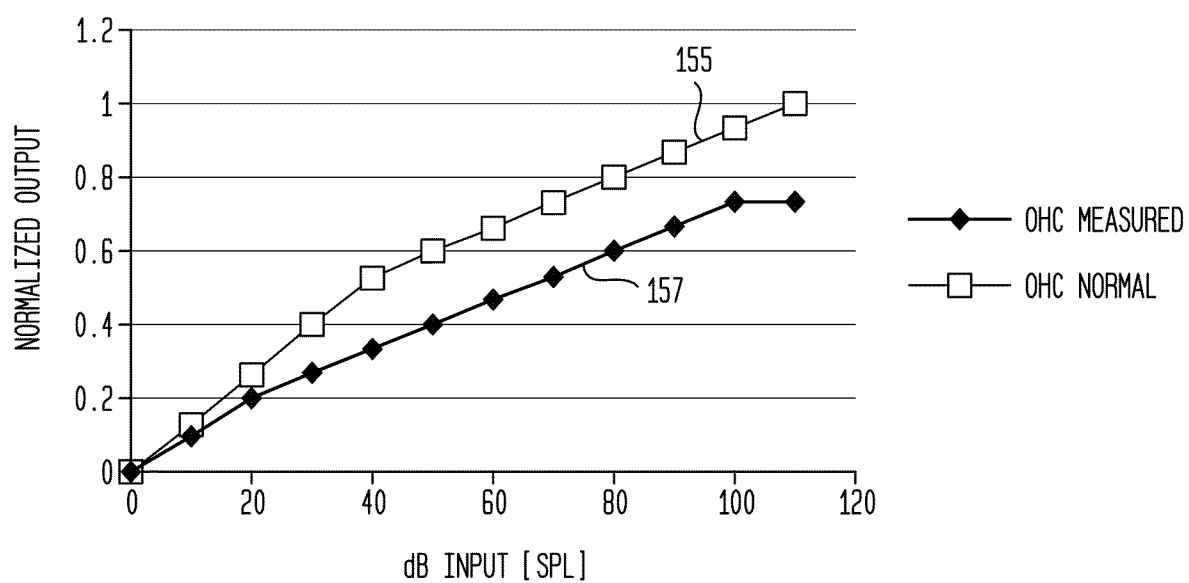
FIG. 5B is a graph illustrating measured outer hair cell (OHC) function outputs and normal/expected outer hair cell function outputs.

FIGS. 5A and 5B are graphs illustrating further details of example auditory nerve neurophonic outputs and outer hair cell outputs, respectively, that may be used to determine input/output functions in accordance with embodiments presented. More specifically, the graph of FIG. 5A includes a first trace 151 representing the auditory nerve neurophonic outputs determined from a recipient's inner ear responses to an acoustic pure tone having an amplitude that is increased from 0 dB SPL to 100 dB SPL. The graph of FIG. 5A also includes a second trace 153 that illustrates auditory nerve neurophonic outputs that are associated with a normal/normative inner ear. That is, trace 153 represents the output that may be expected from a typical inner ear, while trace 151 represents the outputs that are associated with the inner ear of a specific recipient. The horizontal (X) axis of the graph shown in FIG. 5A represents the increasing level of the acoustic pure tone (i.e., the signal that evokes the corresponding auditory nerve neurophonic responses). The vertical (Y) axis represents the normalized outputs (no units) for the auditory nerve neurophonic.

The graph of FIG. 5B includes a first trace 155 representing the outer hair cell outputs determined from a recipient's inner ear responses to an acoustic pure tone having an amplitude that is increased from 0 dB SPL to 100 dB SPL.

The graph of FIG. 5B also includes a second trace 157 that illustrates outer hair cell outputs that are associated with a normal/normative inner ear. That is, trace 157 represents the output that may be expected from a typical inner ear, while trace 155 represents the outputs that are associated with the inner ear of a specific recipient. Similar to FIG. 5A, the horizontal axis of the graph shown in FIG. 5B represents the increasing level of the acoustic pure tone, while the vertical axis represents the normalized outputs (no units) for the outer hair cell outputs.

Returning to FIG. 4, at 158 the objective acoustic prescription module 144 analyzes the one or more input/output functions generated for the sampled cochlea region for physiological abnormalities (e.g., auditory nerve neuropathy, the presence of a dead region, etc.). More specifically, at 158 the objective acoustic prescription module 144 performs a diagnostic operation to determine, based on the one or more input/output functions, whether the sampled cochlea region is functioning properly (i.e., as expected) in response to acoustic stimulation. If the sampled cochlea region is functioning improperly, then the objective acoustic prescription module 144 may operate to determine why the output is not proper (i.e., determine or classify the cause). In certain embodiments, the analysis for physiological abnormalities is based on an analysis of the auditory nerve neurophonic function relative to the outer hair cell function.

In certain examples, the abnormalities are detected by any mismatch between the expected behavior of the CM and the ANN (e.g., relative to another, relative to normative data, etc.). The process of detecting mismatches can include, in certain examples, a difference measure in either the time or the frequency domain. If the difference measure exceeds a particular tolerance, then the response is classified as abnormal either at a particular frequency or globally.

Physiological abnormalities, if present, can impact the gain that is applied to acoustic stimulation signals at the sampling frequency. For example, if a dead region (i.e., a region where the nerve cells are dead and non-responsive) is identified at a particular frequency, then no output is produced and it is ineffective to amplify sounds at that frequency. Therefore, as described below, identified physiological abnormalities can be used is refine the gain functions, accordingly further personalizing the acoustic prescription for the recipient.

As noted above, a recipient's cochlea is tonotopically mapped and acoustic stimulation is used to stimulate the frequencies below the cross-over frequency. As such, a gain function forming part of an acoustic prescription should cover a number of frequencies below the cross-over frequency. Therefore, a determination is made at 160 as to whether or not input/output functions have been determined for all cochlea regions corresponding to each of a plurality of selected frequencies, where the plurality of selected frequencies are a number of frequencies at which acoustic stimulation signals are to be delivered to the recipient (i.e., a set of frequencies for which gains are needed during acoustic stimulation).

If it is determined at 160 that one or more input/output functions have not been determined for cochlea regions corresponding to each of the plurality of selected frequencies, then at 162 the sampling frequency is changed/advanced to a next one of the selected frequencies. The operations of 154, 156, 160, and 162 are then repeated until it is determined at 160 that one or more input/output functions have been determined for cochlea regions corresponding to all of the plurality of selected frequencies.

Once one or more input/output functions have been determined for cochlea regions corresponding to all of the plurality of selected frequencies, then method 150 proceeds to 164 where one or more loudness models/rules are applied across the plurality of selected frequencies. More specifically, the audiogram for the receipient (i.e., generated at 152) is employed along with the one or more input/output functions and the physiological abnormalities, if present, as inputs to a loudness model (e.g., set of loudness rules) that are, in general, intended to ensure that the fitting gain maximizes speech intelligibility at the same time as keeping overall loudness no greater than that of a normal hearing person. The one or more input/output functions acquired using the objective measures are peripheral to the cochlea function and, as such, generally do not account for the the mid-level and the higher level processing of the recipient's auditory system. These higher levels of auditory processing introduce loudness changes that should be accounted for when setting the gain functions so as to ensure both intelligibility and proper loudness are preserved.

Stated differently, at 164 the input/output functions, audiogram, and the physiological abnormalities are used as inputs to a system, executed at objective acoustic prescription module 144, that accounts for what happens at a higher cognitive level of hearing (i.e., the mid-brain elements, the auditory cortex, etc.). The loudness models can be used to map the electrophysiological measurements to how they might be perceived at the higher cognitive level (the cortex).

Figure 6:
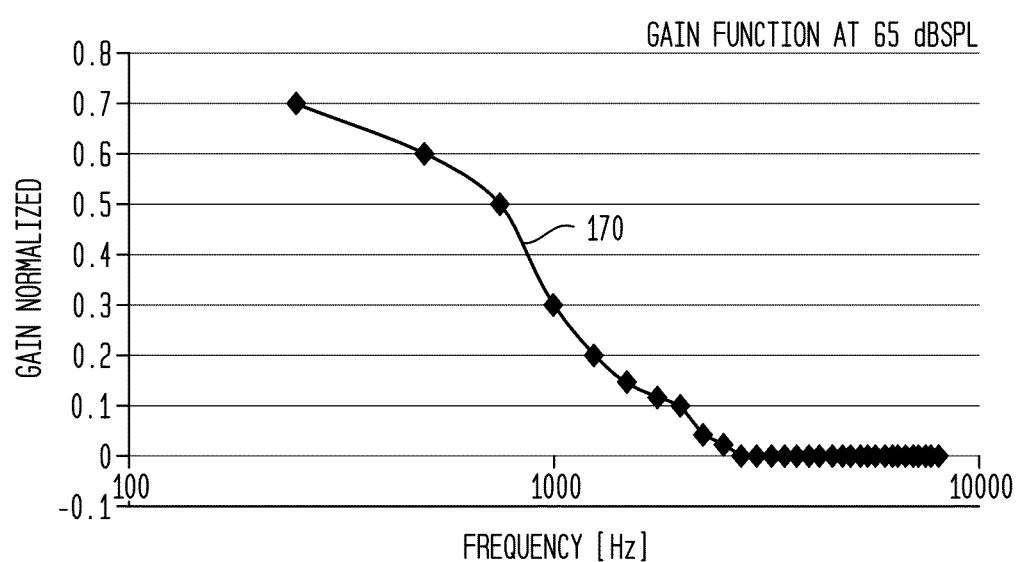
FIG. 6 is a graph illustrating an example gain function generated in accordance with embodiments presented herein.

At 166, following application of the loudness models/rules, one or more gain functions are derived for use in converting sound signal components in acoustic stimulation signals. That is, the one or more gain functions are generated based on the outputs generated as a result of the application of the loudness models/rules to the input/output functions, audiogram, and the physiological abnormalities. FIG. 6 is a graph illustrating an example gain function 170 corresponding to sound signals received at an input level of 65 dB SPL. As shown, the gain applied decreases as the frequency increases (horizontal axis), where the vertical axis represents the normalized gain (no units). The gain function 170 represents an example of device configuration settings generated by the objective acoustic prescription module 144 (i.e., the result is a derivation of gain settings for the acoustic stimulation) and implemented by the electro-acoustic hearing prosthesis 100. In certain examples, different gain functions may be derived for different sound signal levels (i.e., an acoustic prescription may comprise a set of multiple different gain functions).

FIG. 4 has been described with reference to the use of the input/output functions, audiogram, and the physiological abnormalities are inputs to the loudness models/rules (i.e., some system, executed at objective acoustic prescription module 144, that accounts for what happens at a higher cognitive level of hearing). It is to be appreciated that is merely illustrative and that only a subset of the input/output functions, audiogram, and the physiological abnormalities may be used inputs to the loudness models/rules. For example, in certain embodiments, only the input/output functions may be employed as inputs to the loudness models/rules to configure the acoustic hearing prescription. Such embodiments would permit those who cannot provide behavioral feedback with a completely subjective fitting method. Further to this, for such a population, the method may be complemented by the use of other objective measures such as higher evoked potentials such as the EABR and cortical response, sometimes employed for fitting those without the ability to provide behavioral feedback.

It is also to be appreciated that the input/output functions themselves may be employed, without the loudness models, to configure a recipient's acoustic hearing prescription (i.e., to determine one or more gain functions for use by the electro-acoustic hearing prosthesis in conversion of sound signals to acoustic stimulation signals for delivery to the recipient). Such techniques could be refined to include the loudness models and/or other information, such as the audiogram, the physiological abnormalities, etc.

Figure 7:
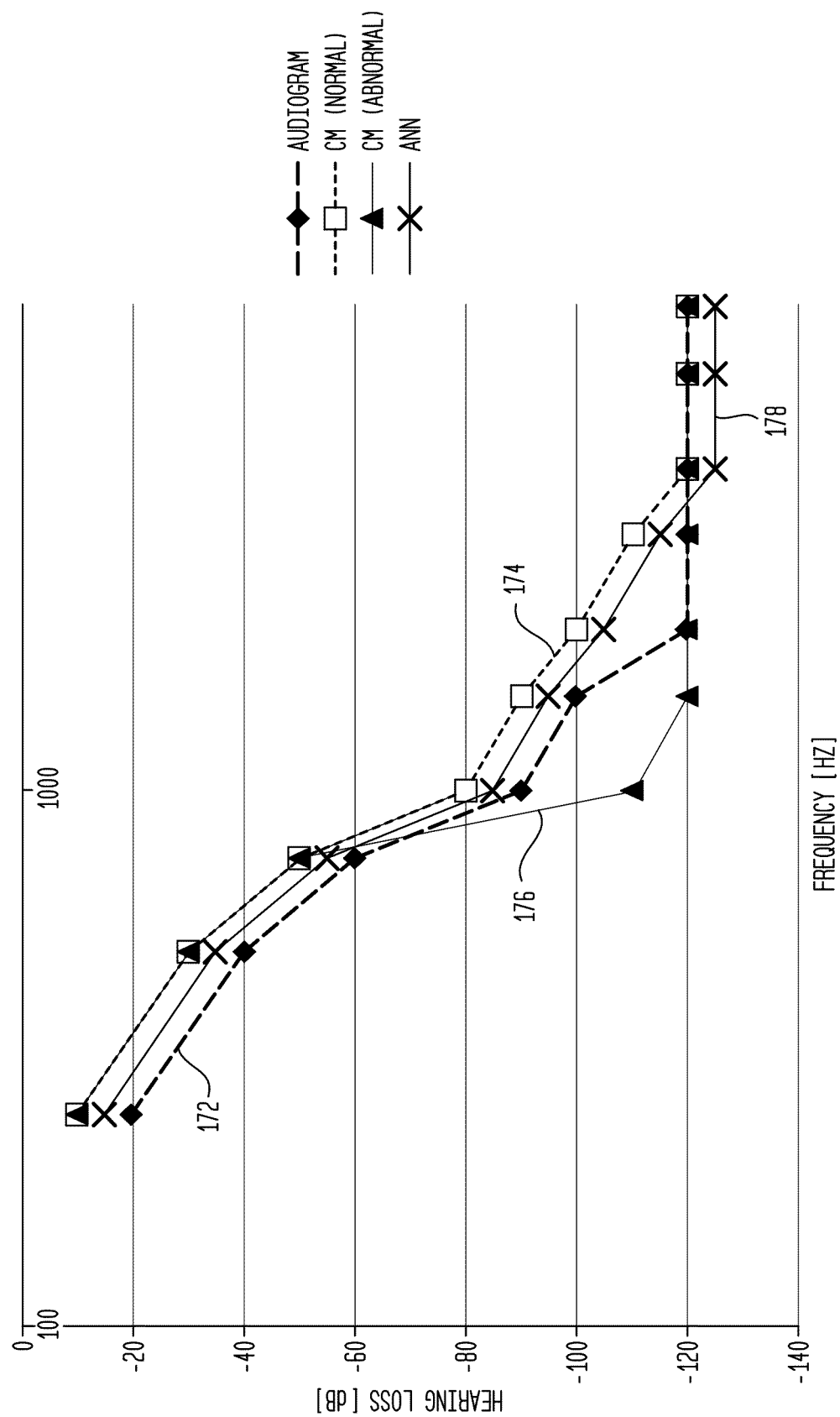
FIG. 7 is a graph illustrating a comparison of hearing thresholds determined from an audiogram and hearing thresholds determined from objective measurements in accordance with embodiments presented herein.

FIG. 7 is a graph illustrating a comparison of the differences in hearing threshold resulting from a conventional audiogram approach versus approaches in accordance with the embodiments presented herein, both for a "normal" physiology and for an "abnormal" physiology. In FIG. 7, the horizontal axis represents increasing frequency, while the vertical axis represents determined hearing loss.

FIG. 7 includes an audiogram trace 172 that illustrates audiogram hearing thresholds determined using an audiogram measurement. As noted above, the audiogram captures the recipient's behavioral hearing thresholds across frequency. As shown, the audiogram trace 172 is steeply sloped in the lower frequencies and indicates a high frequency hearing loss. This type of hearing loss is typical of a recipient who may be a candidate for an electro-acoustic hearing prosthesis (pre-implantation or post-implantation).

Also shown in FIG. 7 are traces 174, 176, and 178. Traces 174 and 176 correspond to the thresholds of the cochloear microphonic for normal and abnormal hearing, respectively, measured in-situ. Trace 178 corresponds to the thresholds of the auditory nerve neurophonic measured in-situ. As shown the profiles of the cochlear microphonic for normal hearing (174) and for the auditory nerve neurophonic (178) are similar to each other, but are different from that of the audiogram (172).

The normal cochlear microphonic (174) is the classification resulting from the comparison of the profiles of the auditory nerve neurophonic and cochlear microphonic, given these track together closely across frequency. The abnormal cochlear microphonic (176) is an alternative classification resulting again from the comparison of the profiles of the auditory nerve neurophonic and cochlear microphonic. In this instance the cochlear microphonic deviates away from the auditory nerve neurophonic, indicating there is an absence or small population of outer hair cells (OHCs) in this region of the cochlea. The presence of a larger auditory nerve neurophonic in these regions of the cochlea (e.g., 750-2000 Hz) suggests a phenomenon called 'off-frequency hearing,' whereby the spread of excitation of regions not associated with the delivered frequency give rise to the behavioral threshold. The physiological explanation of this phenomena is often referred to as a "dead region."

Figure 8:
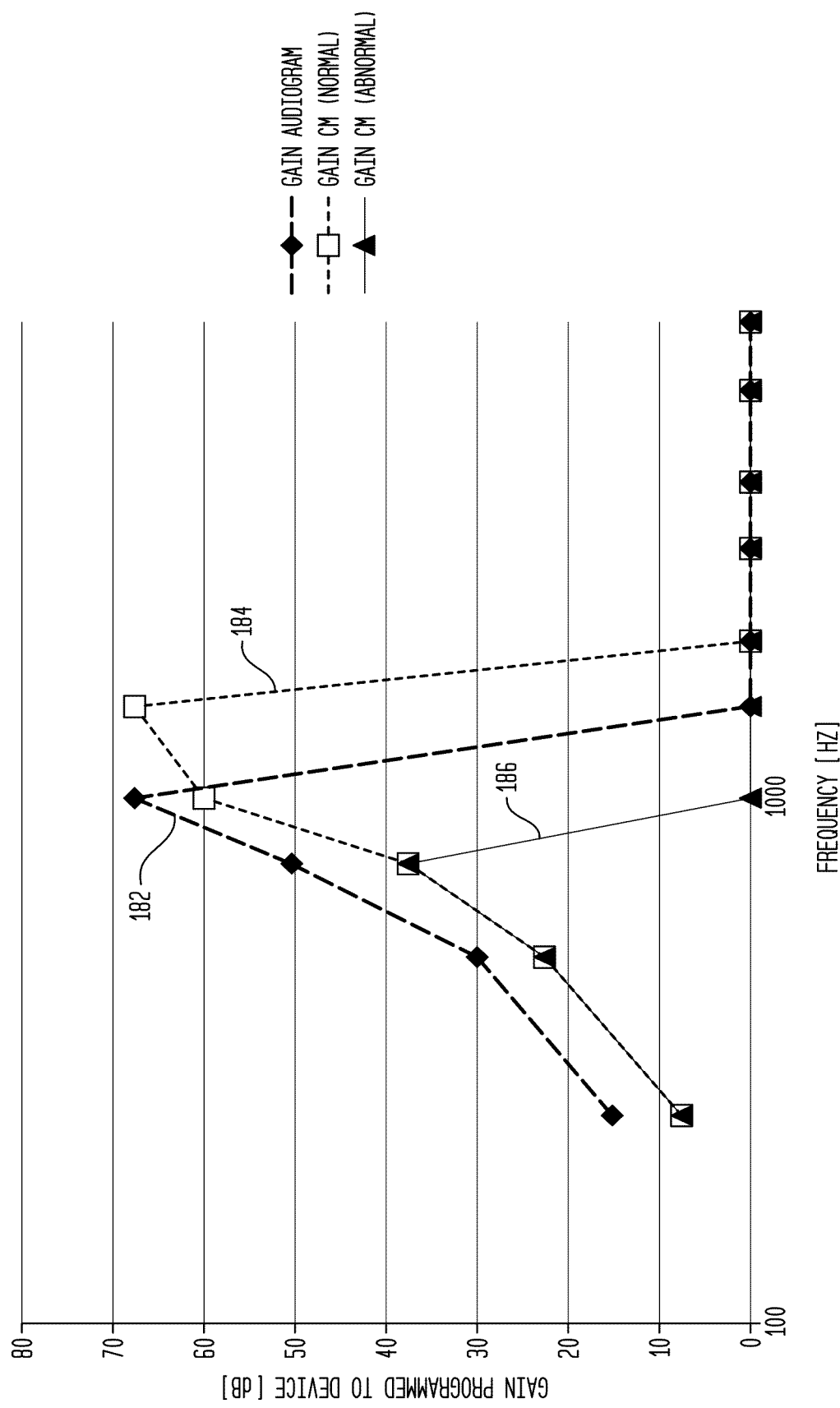
FIG. 8 is a graph illustrating a comparison of gain functions determined from an audiogram and gain functions determined from objective measurements in accordance with embodiments presented herein.

FIG. 8 is a graph illustrating gains calculated for an input level of 50 dBHL. In FIG. 8, the horizontal axis represents increasing frequency, while the vertical axis represents the gain values that would be programmed into a hearing prosthesis for the given frequency.

FIG. 8 includes an audiogram trace 182 illustrating gain values generated based only on an audiogram measurement, a normal cochlear microphonic trace 184 illustrating gain values generated based on cochlear microphonics classified as normal, and an abnormal cochlear microphonic trace 186 illustrating gain values generated based on cochlear microphonics classified as abnormal. As shown, each of the gain functions 184 and 186 are different to that of the conventional audiogram approach represented by 182. In FIG. 8, locations where the gains are set to zero represent the stop point of the acoustic fitting (i.e., gain of zero implies there is no acoustic signal presented at this frequency to the cochlea).

A comparison of the audiogram trace 182 versus the normal cochlear microphonic trace 184 reveals that, due to the cochlear microphonic analysis, one additional frequency channel is added to the recipient's gain profile. The abnormal cochlear microphonic trace 186 is different from the normal cochlear microphonic trace 184 because a comparison of the auditory nerve neurophonic and the cochlear microphonic has revealed the presence of a dead region at certain frequencies of the cochlea. This has translated to these frequencies not being fitted resulting in a large difference between the two fittings (i.e., between 184 and 186). The clinical rationale for not fitting frequencies associated with a dead region is that there is a risk other parts of the cochlea may receive this information (off-frequency) and there is a risk of information being either masked or degraded if these frequencies are amplified. It is not possible to determine such dead regions from the audiogram alone.

Figure 9:
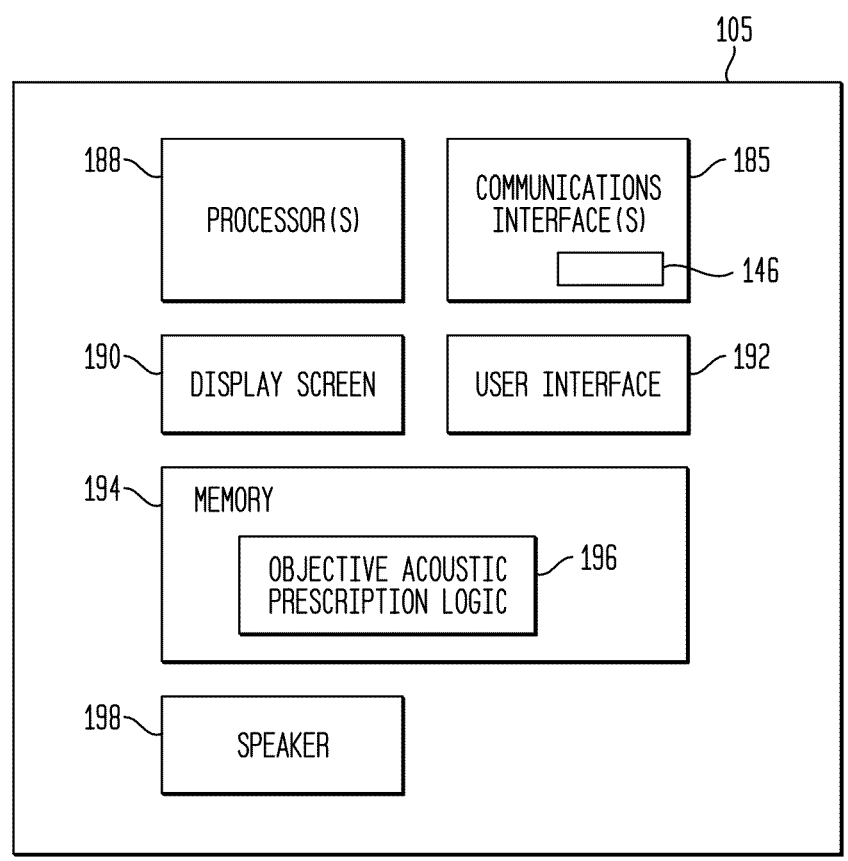
FIG. 9 is a block diagram illustrating one arrangement for an external device forming part of an electro-acoustic hearing prosthesis system in accordance with embodiments presented herein.

FIG. 9 is a block diagram illustrating further details of one arrangement for external device 105 forming part of an electro-acoustic hearing prosthesis system in accordance with embodiments presented herein. As noted above, external device 105 may be, for example, a computing device, such as a remote assistant for the hearing prosthesis, computer (e.g., laptop, desktop, tablet), mobile phone, etc., or other device configured for communication with an electro-acoustic hearing prosthesis, such as prosthesis 100 of FIGS. 1A and 1B.

Referring specifically to the arrangement of FIG. 9, the external device 105 comprises one or more communication interfaces 185, one or more processors 188, a display screen 190, a user interface 192, a memory 194, and a speaker 198. The memory 194 includes objective acoustic prescription logic 196.

The one or more communications interfaces 185 comprise one or more elements for wired or wireless communication with a hearing prosthesis. The communications interfaces 186 may comprise, for example, a short-range wireless transceiver 111, such as a Bluetooth® transceiver that communicates using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. The communications interfaces 186 may also or alternatively comprise a telecommunications interface, a wireless local area network interface, one or more network interface ports, a radio-frequency (RF) coil and RF transceiver, etc.

The display screen 190 is an output device, such as a liquid crystal display (LCD), for presentation of visual information to a user (e.g., surgeon). The user interface 192 may take many different forms and may include, for example, a keypad, keyboard, mouse, touchscreen, display screen, etc. In certain embodiments, the display screen 190 and user interface 190 are integrated to form a touch-screen display.

Memory 194 may comprise one or more tangible (non-transitory) computer readable storage media, such as read only memory (ROM), random access memory (RAM), magnetic disk storage media devices, optical storage media devices, flash memory devices, electrical, optical, or other physical/tangible memory storage devices. The one or more processors 188 are, for example, microprocessors or microcontrollers that execute instructions for the objective acoustic prescription logic 196 stored in memory 194. That is, in one form, the objective acoustic prescription module 144 is implemented as software, sometimes referred to herein as objective acoustic prescription software or logic 196, at external device 105. Therefore, when the objective acoustic prescription logic 196 is executed by the processors 188, the external device 105 is operable to perform the operations described herein with reference to objective acoustic prescription module 144.

FIG. 9 illustrates a specific software implementation for objective acoustic prescription module 144 that makes use of onboard digital signal processors (DSPs) or microprocessors. However, it is to be appreciated that objective acoustic prescription module 144 may have other arrangements. For example, objective acoustic prescription module 144 may be partially or fully implemented with digital logic gates in one or more application-specific integrated circuits (ASICs). Alternatively, the objective acoustic prescription module 144 may be integrated in the electro-acoustic hearing prosthesis 100 (e.g., in sound processing unit 110).

Figure 10:
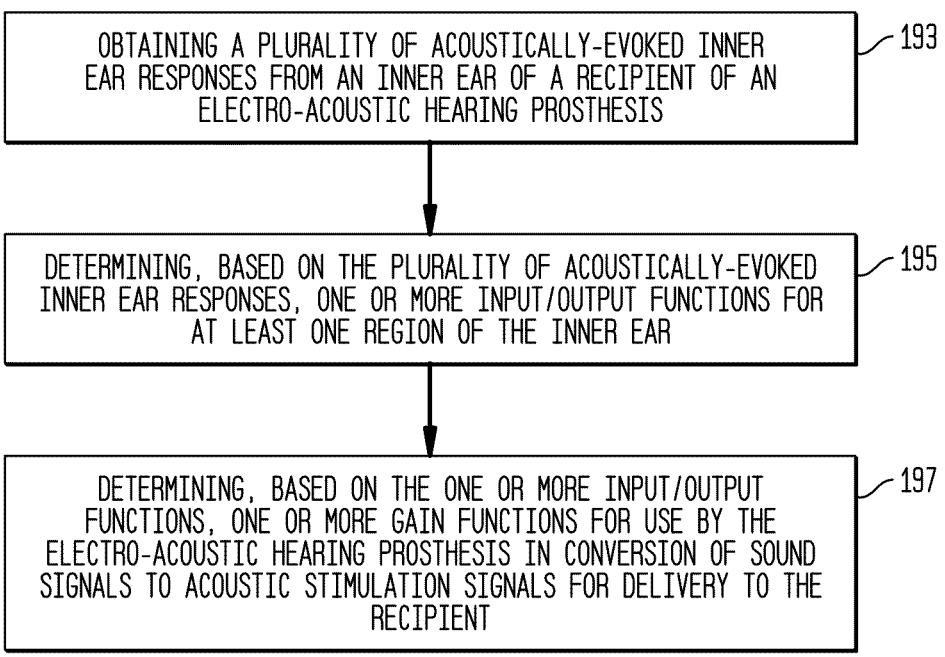
FIG. 10 is a high-level flowchart of a method in accordance with embodiments presented herein.

FIG. 10 is a flowchart of a method 191 in accordance with embodiments presented herein. Method 191 begins at 193 where a plurality of acoustically-evoked inner ear responses is obtained from an inner ear of a recipient of an electro-acoustic hearing prosthesis. At 195, based on the plurality of acoustically-evoked inner ear responses, one or more input/output functions are determined for at least one region of the inner ear. At 197, based on at least the one or more input/output functions, one or more gain functions are determined for use by the electro-acoustic hearing prosthesis in conversion of sound signals to acoustic stimulation signals for delivery to the recipient.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
  delivering one or more sets of acoustic stimulation signals to an inner ear of a recipient of a medical device;
  obtaining, in response to the one or more sets of acoustic stimulation signals, at least one measure of outer hair cell function from a tonotopic region of the inner ear of the recipient;
  determining whether the at least one measure of outer hair cell function differs from an expected measure of outer hair cell function for the tonotopic region of the inner ear to determine whether the at least one measure of outer hair cell function is expected;
  obtaining, in response to the one or more sets of acoustic stimulation signals, at least one measure of auditory nerve function from the tonotopic region of the inner ear of the recipient;
  determining whether the at least one measure of auditory nerve function differs from an expected measure of auditory nerve function for the tonotopic region of the inner ear to determine whether the at least one measure of auditory nerve function is expected;
  determining the inner ear has a physiological abnormality based on one of the at least one measure of auditory nerve function or the at least one measure of outer hair cell function is expected and the other of the at least one measure of auditory nerve function or the at least one measure of outer hair cell function is unexpected; and
  operating the medical device based on determining the inner ear has the physiological abnormality.

2. The method of claim 1, further comprising:
  generating an acoustic prescription for the recipient in response to determining the inner ear has the physiological abnormality, wherein operating the medical device based on determining the inner ear has the physiological abnormality comprises operating the medical device in accordance with the acoustic prescription.

3. The method of claim 1, wherein the at least one measure of outer hair cell function comprises a cochlear microphonic evoked at the tonotopic region of the inner ear.

4. The method of claim 1, further comprising:
  obtaining, in response to the one or more sets of acoustic stimulation signals, a cochlear summating potential from the tonotopic region of the inner ear of the recipient.

5. The method of claim 1, wherein the at least one measure of auditory nerve function comprises an auditory nerve neurophonic evoked at the tonotopic region of the inner ear.

6. The method of claim 1, wherein delivering the one or more sets of acoustic stimulation signals to the inner ear of the recipient of the medical device comprises:
  delivering the one or more sets of acoustic stimulation signals at a selected and substantially constant frequency.

7. The method of claim 1, wherein delivering the one or more sets of acoustic stimulation signals to the inner ear of the recipient of the medical device comprises:
  incrementally adjusting an amplitude of the one or more sets of acoustic stimulation signals.

8. A system, comprising:
  a receiver configured to deliver acoustic stimulus;
  at least one recording electrode configured to measure physiological potentials of an inner ear of a patient in response to the acoustic stimulus; and
  one or more processors configured to:
    obtain at least one cochlear microphonic evoked at a tonotopic region of the inner ear of the patient;
    obtain at least one auditory nerve neurophonic evoked at the tonotopic region of the inner ear of the patient;
    determine whether the at least one cochlear microphonic differs from an expected cochlear microphonic for the tonotopic region of the inner ear of the patient;
    determine whether the at least one auditory nerve neurophonic differs from an expected auditory nerve neurophonic for the tonotopic region of the inner ear of the patient; and
    determine a treatment for the inner ear based on a comparison of any differences between the at least one cochlear microphonic and the expected cochlear microphonic with any differences between the at least one auditory nerve neurophonic and the expected auditory nerve neurophonic.

9. The system of claim 8, wherein the one or more processors are configured to:
  determine the treatment for the inner ear in response to there being a difference between the at least one cochlear microphonic and the expected cochlear microphonic and there being no difference between the at least one auditory nerve neurophonic and the expected auditory nerve neurophonic.

10. The system of claim 8, wherein the one or more processors are configured to:
determine the treatment for the inner ear in response to there being no difference between the at least one cochlear microphonic and the expected cochlear microphonic and there being a difference between the at least one auditory nerve neurophonic and the expected auditory nerve neurophonic.

11. The system of claim 8, comprising an amplifier configured to amplify the physiological potentials measured by the at least one recording electrode for obtaining the at least one cochlear microphonic and the at least one auditory nerve neurophonic at the one or more processors.

12. The system of claim 8, wherein the treatment comprises at least one of an input/output for the inner ear or a gain function for the inner ear.

13. A method, comprising:
obtaining at least one cochlear microphonic evoked at a tonotopic region of an inner ear of a patient;
obtaining at least one auditory nerve neurophonic evoked at the tonotopic region of the inner ear of the patient;
comparing the at least one cochlear microphonic to an expected cochlear microphonic for the tonotopic region of the inner ear to provide a first comparison result;
comparing the at least one auditory nerve neurophonic to an expected auditory nerve neurophonic for the tonotopic region of the inner ear to provide a second comparison result;
comparing the first comparison result with the second comparison result; and
determining a treatment based on comparison between the first comparison result and the second comparison result.

14. The method of claim 13, further comprising:
delivering one or more sets of acoustic stimulation signals to the inner ear of the patient, wherein the at least one cochlear microphonic and the at least one auditory nerve neurophonic are obtained in response to the one or more sets of acoustic stimulation signals.

15. The method of claim 14, wherein delivering the one or more sets of acoustic stimulation signals to the inner ear of the patient comprises:
delivering the one or more sets of acoustic stimulation signals at a selected and substantially constant frequency while incrementally adjusting an amplitude of the one or more sets of acoustic stimulation signals.

16. The method of claim 13, wherein determining the treatment based on the comparison between the first comparison result and the second comparison result comprises:
generating an acoustic prescription in response to a difference between the first comparison result and the second comparison result.

17. The method of claim 16, wherein the first comparison result comprises a difference between the at least one cochlear microphonic and the expected cochlear microphonic, and the second comparison result comprises a match between the at least one auditory nerve neurophonic and the expected auditory nerve neurophonic.

18. The method of claim 16, wherein the first comparison result comprises a match between the at least one cochlear microphonic and the expected cochlear microphonic, and the second comparison result comprises a difference between the at least one auditory nerve neurophonic and the expected auditory nerve neurophonic.

19. The method of claim 13, wherein the treatment comprises electrical stimulation at frequencies below a frequency corresponding to the tonotopic region.

20. The method of claim 19, wherein the treatment comprises acoustic stimulation at frequencies above the frequency corresponding to the tonotopic region.

* * * * *